United States Patent [19]

Kersten et al.

[11] Patent Number: 5,466,725
[45] Date of Patent: * Nov. 14, 1995

[54] ANTI-VIRAL MATERIALS

[75] Inventors: Jean Kersten, Villers St. Amand.; Yves Delmotte, Tertre, both of Belgium

[73] Assignee: Baxter International, Inc., Deerfield, Ill.

[*] Notice: The portion of the term of this patent subsequent to Jan. 26, 2010, has been disclaimed.

[21] Appl. No.: 802,350

[22] Filed: Dec. 4, 1991

Related U.S. Application Data

[63] Continuation-in-part of Ser. No. 759,695, Sep. 9, 1991, Pat. No. 5,181,276, which is a continuation of Ser. No. 484,137, Feb. 22, 1990.

[51] Int. Cl.$^6$ .......................... A01N 25/08; A01N 25/34; C08L 27/06
[52] U.S. Cl. ............................................ 523/122; 424/404
[58] Field of Search ................................. 424/402, 405, 424/409, 411; 2/161 R, 167, 168; 252/52 A, 106, 132, 174.21, 174.23, DIG. 1; 514/715, 717, 724, 730, 941, 975; 524/567, 569

[56] References Cited

U.S. PATENT DOCUMENTS

| | | | |
|---|---|---|---|
| 1,970,578 | 8/1934 | Schoeller et al. | 558/48 |
| 2,774,709 | 12/1956 | Mayhew et al. | 514/747 |
| 4,040,997 | 8/1977 | Van Dommo et al. | 524/178 |
| 4,544,694 | 10/1985 | Bower et al. | 524/385 |
| 4,581,028 | 4/1986 | Fox et al. | 623/2 |
| 4,612,337 | 9/1986 | Fox et al. | 514/38 |
| 4,867,972 | 9/1989 | Girardieau et al. | 424/409 |

OTHER PUBLICATIONS

Helenius A. and K. Simons, "Solubilization of Membranes By Detergents," Biochimica et Biophysica Acta, 415 (1975), pp. 29–79.

Byrdson, J. A., "Relation of Structure to Chemical Properties," Plastics Materials, Third Edition, pp. 83–89.

Chvapil, M., J. B. Ulreich, K. O'Dea, K. Betts, and W. Droegemueller, "Studies on Nonoxynol–9. III. Effect on Fibroblasts and Spermatozoa," Fertility and Sterility, vol. 33, No. 5, May 1980, pp. 521–525.

DeGroot–Kosolcharoen, J. and J. M. Jones, "Permeability of Latex and Vinyl Gloves to Water and Blood," American Journal of Infection Control, vol. 17, No. 4, Aug. 1989, pp. 196–201.

Greef, R. A., E. A. Setzkorn, and W. D. Leslie, "A Colorimetric Method for the Determination of Parts/Million of Nonionic Surfactants," The Journal of the American Oil Chemists' Society, vol. 42, Mar. 1965, pp. 180–185.

Griffin, W. C., "Classification of Surface–Active Agents by HLB," Journal of the Society of Cosmetic Chemists, presented at the Oct. 11, 1949 meeting, pp. 311–326.

Paulssen, J., T. Eidem, and R. Kristiansen, "Perforations in Surgeons' Gloves," Journal of Hospital Infection, (1988), 11, pp. 82–85.

Newspaper articles: published between Jun. 1991 and Feb. 1992 relating to Baxter's Anti–AIDS glove (translated from French—including certificate of translation).

Baxter brochures in French, German, and Dutch published Jun. 1991.

Primary Examiner—Thurman K. Page
Assistant Examiner—C. Azpuru
Attorney, Agent, or Firm—Kay H. Pierce

[57] ABSTRACT

The present invention relates to anti-viral materials. These anti-viral materials have a pool of anti-viral agents acting in cooperation with certain plasticizers to maintain and increase the anti-viral agents efficacy. These anti-viral materials may be used to make surgical gloves, condoms, surgical clothes, surgical operative fields, finger stalls, aprons, bibs and caps.

4 Claims, 8 Drawing Sheets

ANTI-VIRAL MATERIALS

RELATED APPLICATIONS

This application is a continuation in part of U.S. Ser. No. 07/759,695, filed Sep. 9, 1991 now U.S. Pat. No. 5,181,276 which is a continuation of U.S. Ser. No. 07/484,137 filed Feb. 2, 1990 now abandoned.

BACKGROUND OF THE FIELD

The present invention relates to anti-viral materials. These materials have a pool of anti-viral agents acting in cooperation with certain plasticizers to maintain and increase the anti-viral agents efficacy.

DESCRIPTION OF THE PRIOR ART

It is known that, for manufacturing devices from a molten blend of polymer, it is suitable to add same additives such as plasticizer(s) and antioxidant(s).

It is also known to cover devices with a layer containing an antibacterial agent. For covering such devices, a composition containing a polymer, a solvent of said polymer and an antibacterial agent is prepared, said composition being then applied on the surface of the device so that, after drying, the device is provided with an antibacterial polymeric layer. Such devices are expensive and have antibacterial properties only on one surface thereof.

It is known to add to molten polyvinyl chloride benzoate of sodium or mercury salts for avoiding a microbial growth on said polymer; however, such additives are toxic for the health so that the use thereof has to be proscribed.

NONOXYNOL-9 (α-(nonylphenyl-w-hydroxypoly (oxy-1-2,ethanediyl), a nonionic surfactant has been described as an inhibitor of the growth of herpes simplex virus and HTLV-III. NONOXYNOL-9 (α-(nonylphenl-w-hydroxypoly(oxy-1-2, ethanediyl), has also been used in spermicides. See Fox, U.S. Pat. No. 4,581,028.

SUMMARY OF THE INVENTION

This invention provides polymeric viral resistant material made by the process comprising: mixing a molten blend of a polymer, a compound having a Hydrophilic Lipophilic Balance of between 12 and 20, the said compound consisting of: $R_1-O-((CH_2)a_i-O)n-R_2$ where $R_1$ is a saturated or unsaturated hydrocarbon radical, the constituent elements selected from the group consisting of carbon, hydrogen or oxygen; $a_i$ is, for i=to $_n$, an integer greater or equal to 2; $R_2$ is an organic radical, the constituent elements selected from the group consisting of carbon, hydrogen or oxygen. n is an integer selected so that the Hydrophilic Lipophilic Balance of said compound is between 12 and 20, said compound comprising at least 1% of said material, the improvement comprising adding a sufficient amount of a plasticizer to increase the viricidal activity of the compound.

The molten blend of this invention may thus, for example, be: extruded, injected or dip moulded so as to manufacture viral-resistant materials or devices; or sprayed on materials or devices so as to provide said materials or devices with a viral resistant layer.

The invention also relates to anti-viral materials made into: surgical gloves, condoms, surgical clothes, surgical operative fields, finger stalls, aprons, bibs, caps, etc, manufacturers for example by injecting into a mould a molten blend of a polymer mixed with the compound. The invention relates to composition of polymer(s) containing the compound, the compounds or/and compositions being suitable for the manufacture of viral resistant devices according to the invention.

DETAILED DESCRIPTION OF THE DRAWINGS

DETAILED DESCRIPTION OF THE INVENTION

Figure 1:
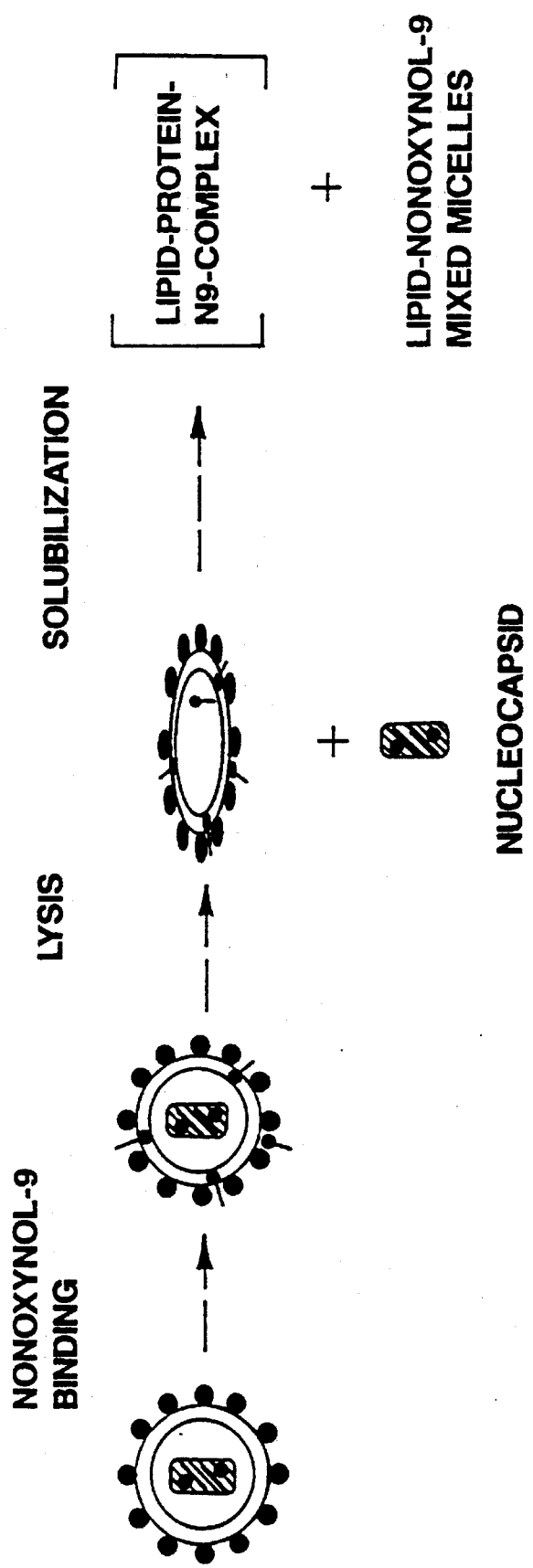
FIG. 1 shows a schematic representation of the effect of NONOXYNOL-9 (α-(nonylphenyl-w-hydroxypoly (oxy-1-2, ethanediyl), on an enveloped virus.

The present invention relates to the discovery that certain plasticizers facilitate the ability of a nonionic detergent to destroy an enveloped virus. As shown in FIG. 1 a nonionic detergent, such as NONOXYNOL-9 (α-(nonylphenyl-w-hydroxypoly (oxy-1-2, ethanediyl), binds to the viral membrane and causes a change in the membrane permeability. The bound detergent acts as a water pump by increasing the intracellular pressure which in turn causes membrane disruption and the destruction of the membrane components. The detergent functions as a wedge, that binds and splits the cell membrane, destroying the natural orientation of the virus membrane components. Helenius, *Solubilization of Membranes by Detergents*, Biochemica et Biophysica Acta, 415:29–79 (1975) (hereby incorporated by reference).

Additionally, it has been discovered that certain nonionic detergents such as DINP (di iso nonylphthalate) plasticizer lipidic membranes. The penetration of the lipophilic branch of an anti-viral compound such as NONOXYNOL-9 (α-(nonylphenyl-w-hydroxypoly (oxy-1-2,ethanediyl) in the cell membrane will be facilitated by the pre-plasticizing effect of the plasticizer on lipidic cell membranes.

Nonionic detergents are compounds of the general formula:

$$R_1-O-((CH_2)a_i-O)_n-R_2 \tag{1}$$

where $R_1$ is a saturated or unsaturated hydrocarbon group;

$a_i$ is, for i=1 to n, an integer greater or equal to 2;

$R_2$ is an organic group possibly substituted, and is an integer selected so that the HLB of said compound is comprised between 12 and 20.

Since the compounds of formula in which $R_1$, $R_2$, $a_i$ and n have the above given meanings does not affect the polymer network properties, such as tensile strength, elasticity modules, etc up to 10% or even more of said compounds may be added.

These compounds may be characterized by a Hydrophile-Lipophile Balance (HLB) as taught by GRIFFIN, W. C., J. Soc. Cosmet. Chem.1, 311–326 (1949). Such compounds are, for example, alkylphenoxypoly (ethyleneoxy) ethanol and more specifically nonylphenoxypoly (ethyleneoxy) ethanol (ANTAROX (nonylphenoxy poly(ethyleneoxy) ethanol), ANTAROX CO-630, and NONOXYNOL-9

(α-(nonylphenyl-w-hydroxypoly(oxy- 1-2, ethanediyl)), Triton X-100 (Boehringer Mannheim). Methods for the manufacturing of such compounds are given for example, in U.S. Pat. Nos. 1,970,578 and 2,774,709.

Certain plasticizers can be used to increase the incorporation of nonionic detergent into a polymer and also to increase the efficacy of the nonionic detergent. To act as a plasticizer, within the scope of this invention the plasticizer must have a molecular weight of at least 300. It should have a similar solubility parameter to that of the polymer. The solubility parameters can be determined by Small's method. Small, Relation of Structure to Chemical Properties, J. Appl. Chem., 3:71 (1953). If the polymer has any tendency to crystallize it should be capable of some specific interaction with the polymer. It should not be crystalline solid at ambient temperature unless it is capable of specific interaction with the polymer.

For example, from Table 5.6, of Small it can be seen that plasticizers for polyvinyl chloride such as the octyl phthalates, triolyl phosphate and dioctyl sebacate have solubility parameters within the 1 c.g.s unit of that the polymer. On the other hand, dimethyl phthalate and the paraffinic oils which are not polyvinyl chloride plasticizers fall outside the range. Most common acids used are:
ACETIC ACID
CITRIC ACID
ACONITIC ACID
TARTRIC ACID
ADIPIC ACID
SEBACIC ACID
TRIMELLITIC ACID
PHTHALIC ACID, etc.

The chain length of the alcohol molecules involved in the chemical reaction with a particular type of acid will give a compound which has to meet the requirements to act as a plasticizer.

Practically, phthalates prepared from alcohols with about eight carbon atoms are by far the most important class and probably constitute about 75% of the plasticizers used, more known as DEHP (Di ethyl Hexyl phthalate).

In the glove formulation, we use the di-iso nonyl phthalate (DINP), which formula is described here under.
DINP: 1,2 BENZENEDICARBOXYLIC ACID, DI NONYL ESTER PHTHALIC ACID, DINONYL ESTER
FORMULA: C26H4204

Polymers which may be used in said method are ethylene-vinyl acetate, ethylene-ethyl acrylate, ethylene-methyl acrylate, ethylene-butyl acrylate, polyvinylchloride, polyesters, polystyrene, polyamide, polycarbonate, polyurethane, and other thermoplastic rubbers.

The $C_{6-12}$ alkyl group which is used as substituent in para position of the phenyl radical may be selected from the group consisting of linear alkyl group such as n-hexyl, n-heptyl, n-octyl, n-nonyl, decyl, n-undecyl and n-dodecyl and branched alkyl group such as methyl pentyl, methyl heptyl, methyl octyl, methyl nonyl, methyl decyl, methyl undecyl, di-methyl hexyl, 4-(tert-octyl), ethyl propyl.

Preferred alkyl groups are n-octyl, n-nonyl, 4-(tert-octyl), 7-methylheptyl, 6-dimethylhexyl, 8-methyl-octyl, 7-dimethylheptyl.

THERMAL STABILITY TESTS

The stability of blends containing compounds ANTAROX CO-630 (nonylphenoxy poly (ethyleneoxy) ethanol) (normal grade) has been shown by means of the following test.

A sample of polyvinyl chloride has been heated on the following manner:

0 to 3 minutes the sample is hated at 55° C. under nitrogen, from 3 to minutes to 6 minutes the temperature of the sample under nitrogen is increased at a rate of 40° C. per minute, from 6 minutes to 46 minutes (end of the test) the temperature of the sample is maintained at 175° C. and a flow of oxygen is applied on the sample, the thermal response of which is studied by means of Perkin Elmer Thermal Analysis System.

Figure 2:
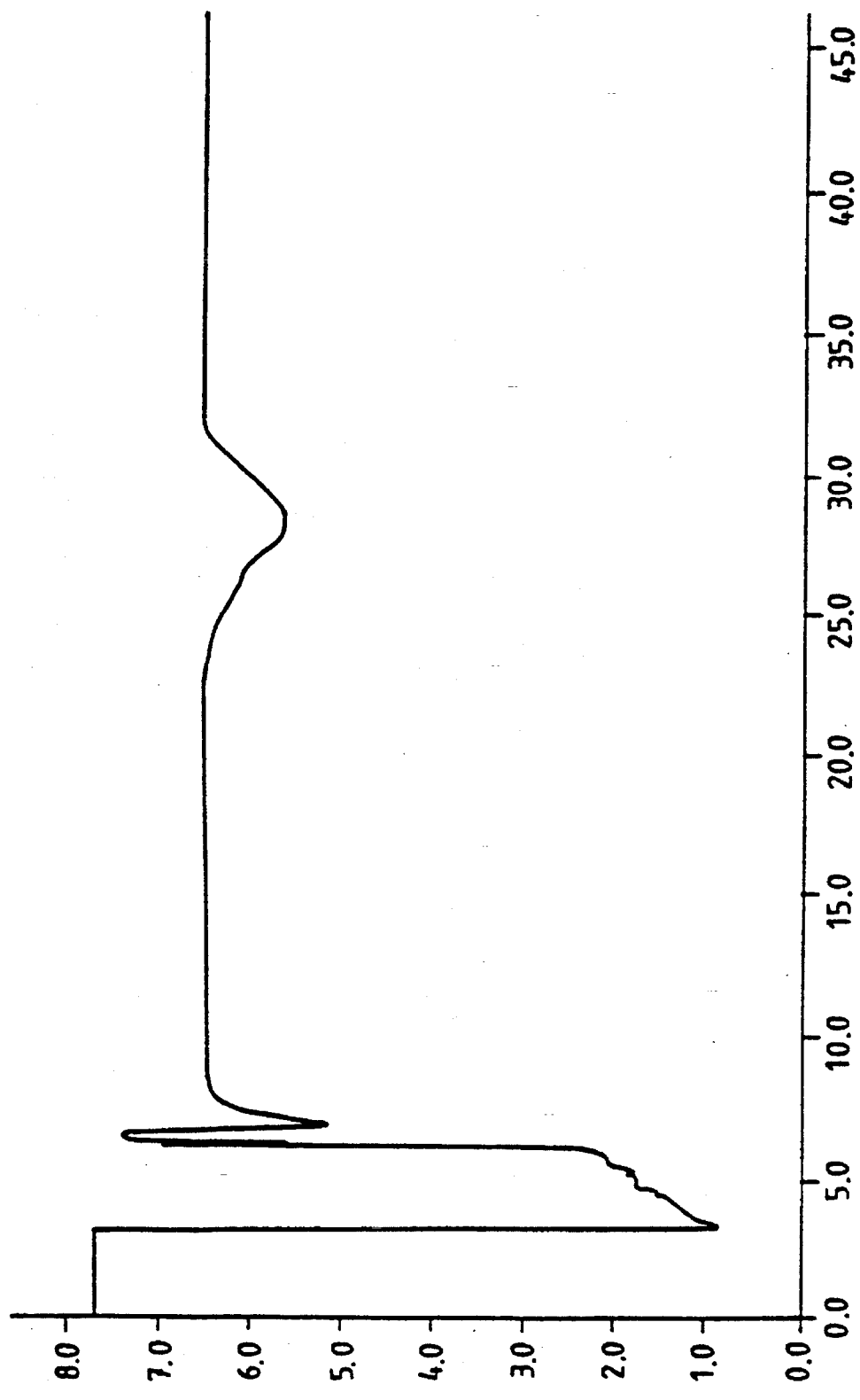
FIGS. 2, 3 and 4 show the stability of polyvinylchloride at 175° C.
Figure 3:
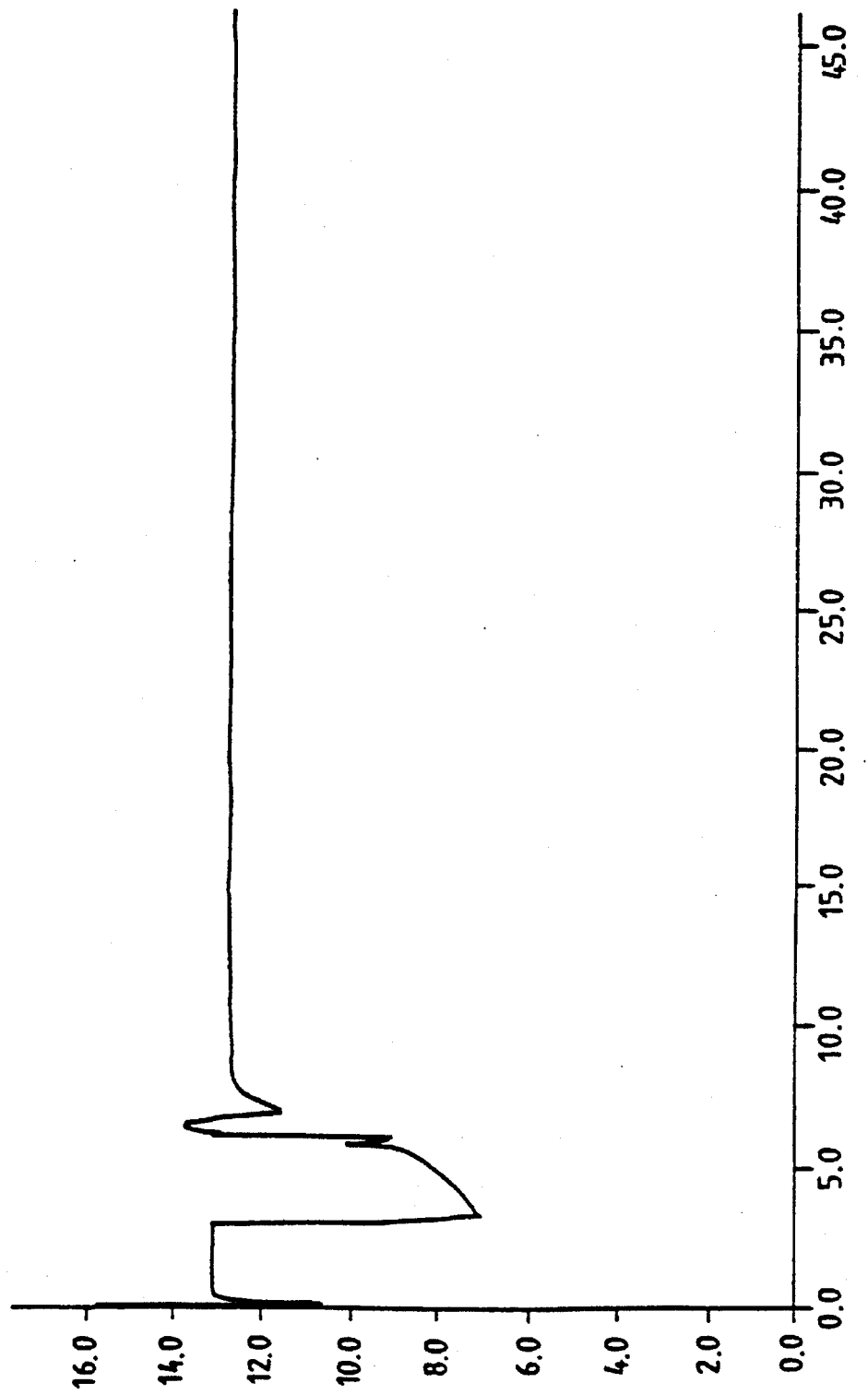
Figure 4:
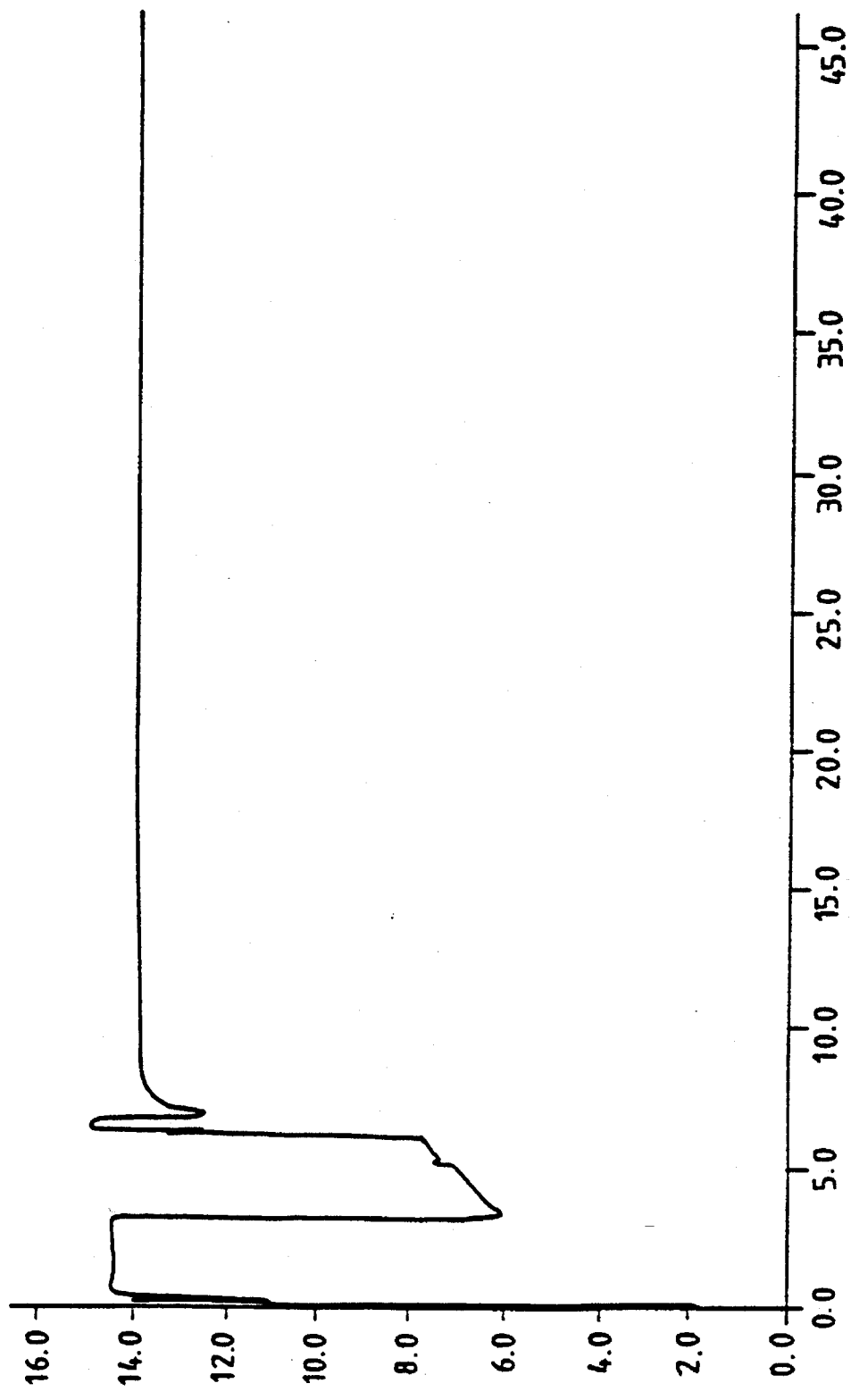

FIGS. 2 to 4 show the thermal response of polyvinyl chloride sample i.e. the heat flow (mW) required for heating the sample (P) or for the melting thereof (Q) or for maintaining a temperature of 175° C. (R) after a time of X minutes.

If a variation of heat flow occurs while maintaining a temperature of 175° C., it means that the sample is oxidized or degradated.

FIG. 2 shows the thermal response of a polyvinyl chloride sample, with the standard plasticizer (di iso nonyl phthalate) while FIG. 3 and FIG. 4 show the influence of replacing the standard plasticizer with an equivalent amount of ANTAROX CO-63 (nonylphenoxy poly (ethyleneoxy) ethanol), respectively for 5 and 10% of the formulation concentration.

It appears from these figures that the addition of ANTAROX CO-630 (nonylphenoxy poly(ethyleneoxy) ethanol), increases the stability of the vinyl chloride phhalate sample. It means also that ANTAROX CO-630 (nonylphenoxy poly(ethyleneoxy) ethanol), is stable at temperature of 175° C. so that said compound may be used in usual techniques such as polymer injection, extrusion, without any degradation.

It has been found that these compounds have viricidal action against Hepatitis B, Hepatitis C and D, Herpes Simplex I and II, other enveloped virusus and AIDS (HIV-I, HIV-II). The compounds are stable at temperature of about 200° C.

In a method according to the invention, nonionic detergents are mixed with a plasticizer before being added to a molten polymer. When manufacturing for example, disposable gloves, the nonionic detergent will be distributed between the surface and the polymer matrix. Therefore, materials made according to this invention provide an antiviral contact protection.

Additionally, in the case of a polymer based product the polymer network works as a reservoir for the nonionic detergent, releasing on demand, an effective concentration of nonionic detergent on both sides of the polymer film. This process provides two benefits: 1) by releasing nonionic detergent to the outside of the polymer film. Detergent that may have been removed by surface contact is replaced. Second, as detergent is released to the inside, protection is provided from the many pinholes that developed in a thin polymer film.

EXAMPLES OF MANUFACTURE 95 kg of liquid PLASTISOL, (a blend containing 45% of polyvinyl chloride, the rest essentially di iso non phthalate) is mixed with 5 kg of ANTAROX CO-630 (nonylphenoxypoly (ethyleneoxy) ethanol). The film contained 35% DINP (di iso nonylphthalate) and 5% of NONOXYNOL-9 (α-(nonylphenyl-w-hydroxypoly (oxy-1-2,ethanediyl). The composition has been cast so as to produce film samples for mechanical tests, after gelification at 175° C.

During the mixing of ANTAROX CO-630 (nonylphenoxypoly (ethyleneoxy) ethanol), with the PLASTISOL, no phase separation was observed. The tensile strength of samples was estimated by tests performed with a rate of 200 mm/min. A surface migration of ANTAROX CO-630 (nonylphenoxypoly (ethyleneoxy) ethanol), was observed for the films, the thickness of which was approximative 130 microns.

In a same manner, films samples were manufactured from a composition containing 90 kg of PLASTISOL and 10 kg of ANTAROX CO-630 (nonylphenoxypoly (ethyleneoxy) ethanol). This film contained 30% DINP (di iso nonylphthalate) and 10% NONOXYNOL-9 (α-(nonylphenyl -w-hydroxypoly (oxy-1-2,ethanediyl). A surface migration was also observed for the gloves, the thickness of which was about 130 microns.

The mechanical properties of the casted film samples are summarized in the following table. For comparison purpose said table contains also mechanical properties of samples made only from PLASTISOL. This film had 40% DINP (di iso nonylphtalate).

TABLE 1

| | PLASTISOL | PLASTISOL + 5% ANTAROX ESTIMATED | PLASTISOL + 10% ANTAROX ESTIMATED |
| --- | --- | --- | --- |
| Tensile Strength N/mm$^2$ | 8.1 | 6.94 | 5.9 |
| Elongation % | 217 | 241 | 243 |

When using gloves containing ANTAROX CO-630 (nonylphenoxypoly (ethyleneoxy) ethanol), no allergic reaction of the users was observed.

The gas permeability of polyvinylchloride with or without Antarox CO-630 (nonylphenoxypoly (ethyleneoxy) ethanol), has also been studied.

For this study, samples are set in a measuring chamber comprising two parts, the lower of which being the circulation and sampling system while the upper part is the gassing chamber.

The working gas was constituted of respectively one third of carbon dioxide ($CO_2$), one third of oxygen ($O_2$) and one third of nitrogen ($N_2$), said gas flowing in the upper part.

Said gas passes through the polyvinylchloride film and is periodically swept by helium gas (vector gas) to the detector where it is quantified.

Figure 5:
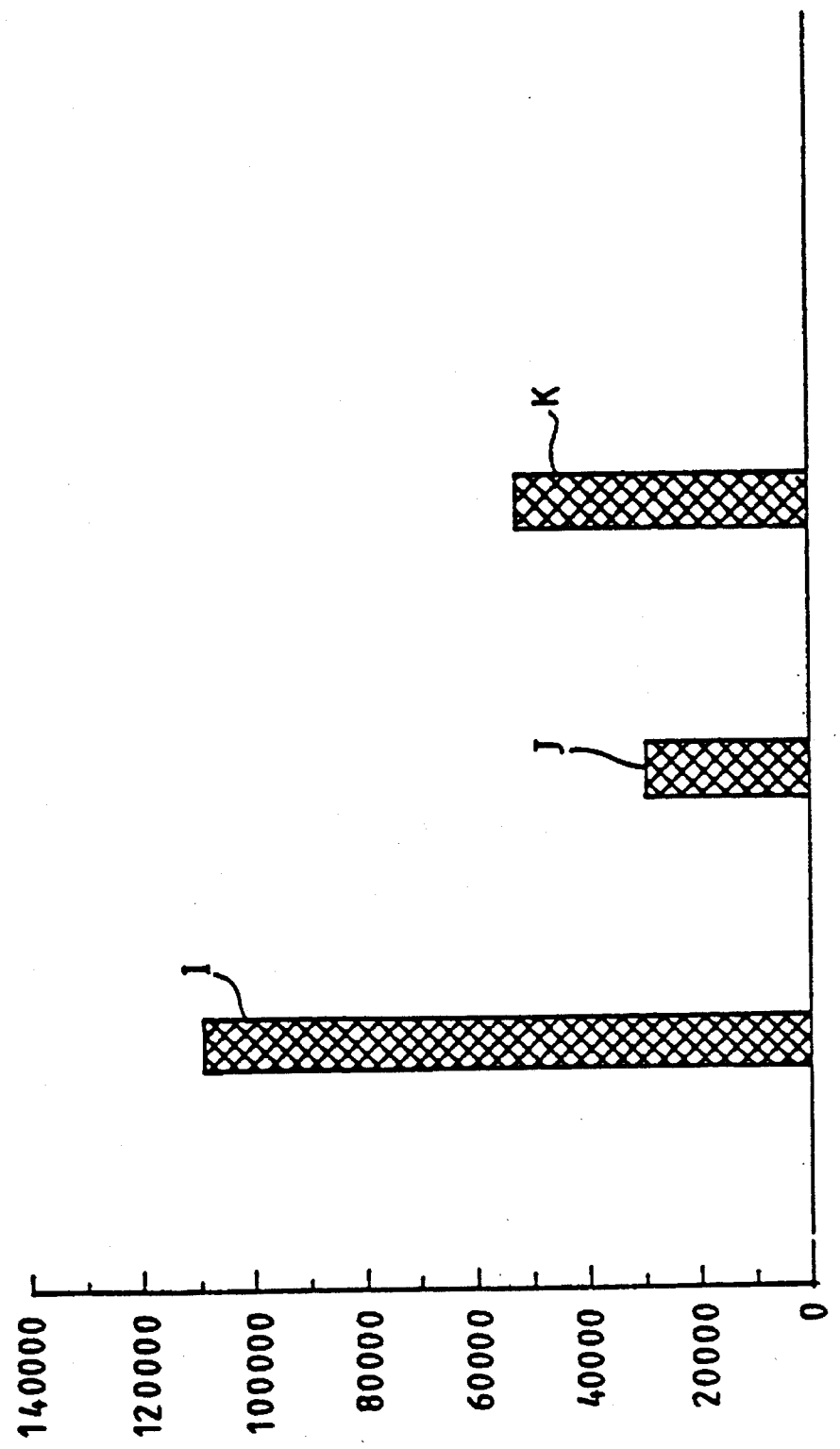
FIGS. 5 and 6 show permeabilities of polyvinylchloride.
Figure 6:
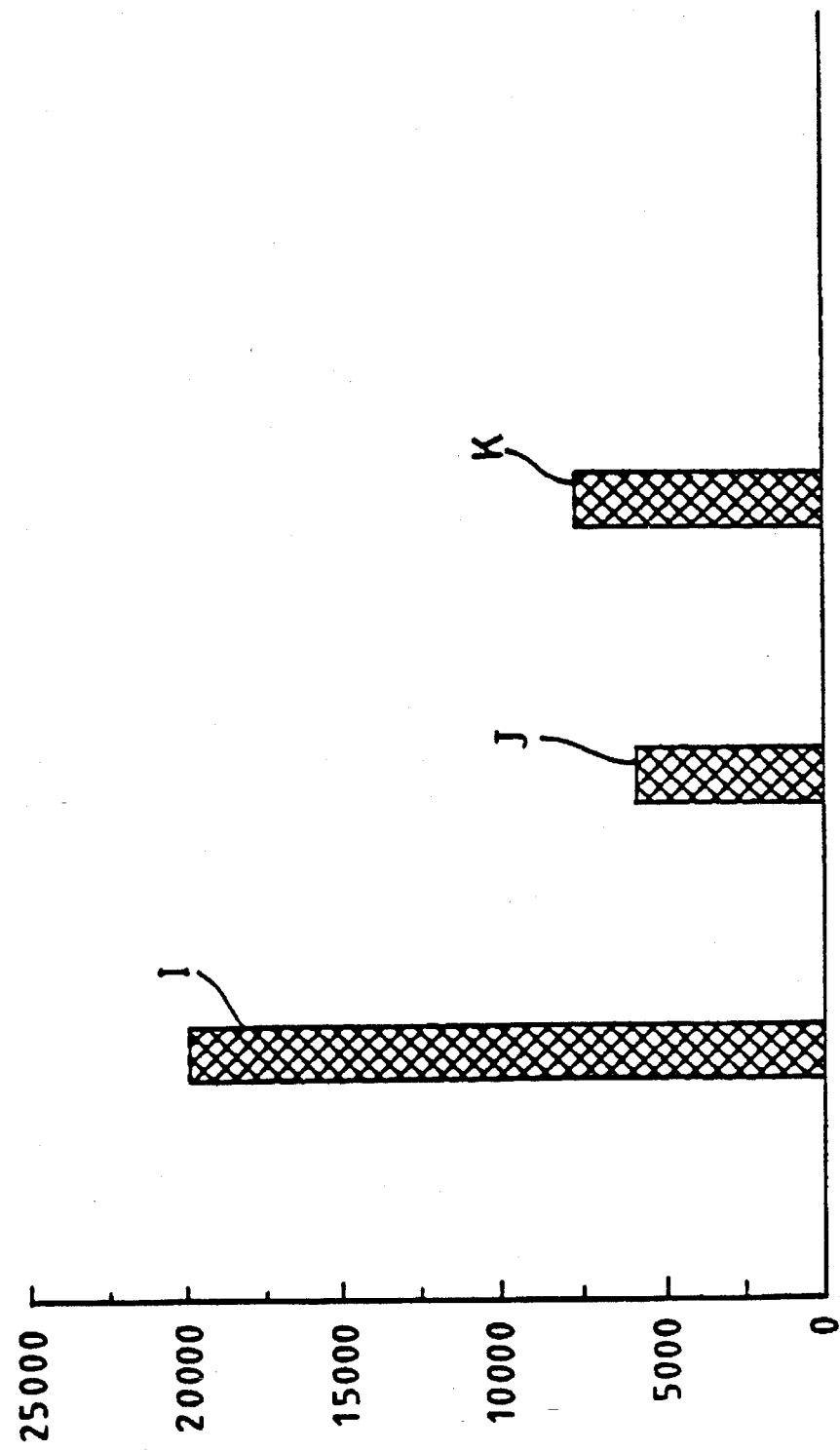

The permeabilities of the films without ANTAROX CO-630 (nonylphenoxypoly (ethyleneoxy) ethanol), (film I, PLASTISOL), of the film containing 5% Antarox CO-630 (nonylphenoxypoly (ethyleneoxy) ethanol), (film J) and of the film containing 10% Antarox CO-630 (nonylphenoxypoly (ethyleneoxy) ethanol), (film K) are given in FIG. 5 for $CO_2$ and in FIG. 6 for $O_2$, said permeabilities being expressed in cm$^3$/day m$^2$atm.

Devices and materials obtained by the process according to the invention are thus effective for making gas barrier.

The gas barrier property of films or materials obtained by the process according to the invention are improved when the composition contains at least 1% of compound(s) of the general formula, preferably between 2 and 10% and more preferably about 5%.

The viscosity of plastisol is about 800 to 1300 cps at temperature comprised between 30 and 35° C. while the viscosity of plastisol containing 10% ANTAROX CO-630 (nonylphenoxypoly (ethyleneoxy) ethanol),is about 920 cps at 32° C.

Example 1—Viricidal Activity of Films

Three films were evaluated: a reference film (polyvinyl chloride film alone), film 1 (polyvinyl chloride film containing 5% NONOXYNOL-9 (α-(nonylphenyl -w-hydroxypoly (oxy-1-2, ethanediyl) and 35% DINP and film 2 (polyvinyl chloride film containing 10% NONOXYNOL-9 (α-(nonylphenl-w-hydroxypoly (oxy-1-2, ethanediyl) and 35% DINP. The viricidal effect as well as the non-permeability to HIV-1 were tested in the viral Oncology Unit of Prof. L. Montagnier at the Pasteur Institute.

Human Immunodeficiency Virus (HIV)

The test virus was completed of HIV-1 infected CEM cell culture supernatant. The titre of the viral supernatants was evaluated after dosage of: the Reverse Transcriptase Activity (RTA) the infectivity for a CEM-C113 cell cloned line. For this study, an experimental HIV virus defined by a total reverse transcriptase activity (RTA) equal to $10^6$ cpm/ml) with a 50% detectable infections titre at the dilution rate $10^{-5}$ after 19 days of culture was used.

Methods

The experimental technique for the three types of films is as follows: Three 60 mm diameter disks of each film was cut. The film was stretched slightly and placed on a petri dish containing three ml of physiological solution. One ml of viral solution was placed on these films (two per test) with a titer of RTA of $10^6$ cpm/ml. The viral solution was allowed to contact each film for 1, 3, 5, 10 and 30 minutes at 20° C. After each contact time one ml viral solution from each film, the three ml physiological solution from the petri dish was collected.

The physiological solution was used to confirm the presence of any viral particles passing through the film membranes (p24/25 antigen estimation). The viral solutions controled the equivalence of the HIV infectivity after the different incubation times to those determined at the start time=0 of the experiment (=potential viricidal activity of the external side containing NONOXYNOL-9 (α-(nonylphenyl -w-hydroxypoly(oxy-l-2, ethanediyl).

Each sample, physiological solution or viral solution diluted or not, was placed in a culture medium with $10^5$ CEM-C113 cells. Every 3 to 4 days the cultures, were tested to determine cell viability (MTT dosage) and the viral production in the culture supernatants (dosage of RTA). Every 6 days the cultures, were tested to determine for the physiological solution samples, the cell viability (MTT dosage) as well as their infectivity (p24/25 antigen dosage).

TECHNIQUE USED FOR DOSAGE

The nonpermeability of the different types of films was determined by the measurement of the p24/25 HIV antigen at time zero and after the 6th day of culture in the physiological solution samples. This method follows the HIV-1 p24/25 Core Profil Elisa from DUPONT. For the viral activity, the viral production is determined by the measurements of the RTA value using the enzymatic dosage by incorporated tritiated thymidine.

VALIDATION

Testing for validation as well as the different trials on the films were performed twice.

The CEM-C113 were grown in a culture medium and treated in the same conditions as for the other samples. This test was considered a negative control of the viral production and will serve as a check for the cells viability.

A virus control solution with a RTA titre of $3\times10^4$ cpm/ml was added to the CEM-C113 cell culture to check the infectious rate of the HIV.

These controls allow for monitoring the cell viability in presence of potential chemical leachables which could be released by tested the films. Therefore, $10^5$ CEM-C113 cells/ml were grown with physiological solution collected on the three types of films after a 30 minute contact time. This was be considered the negative control of the viral production during the experiment.

The HIV infectivity without any contact on polyvinyl chloride films was detected at 50% (3 wells of positive culture versus 6) at a $2\times10^{-5}$ dilution rate and at 100% (6 positive culture wells) until a $2\times10^{-4}$ dilution rate after 20 days' culture. This was considered the positive production control of untreated virus.

Figure 7:
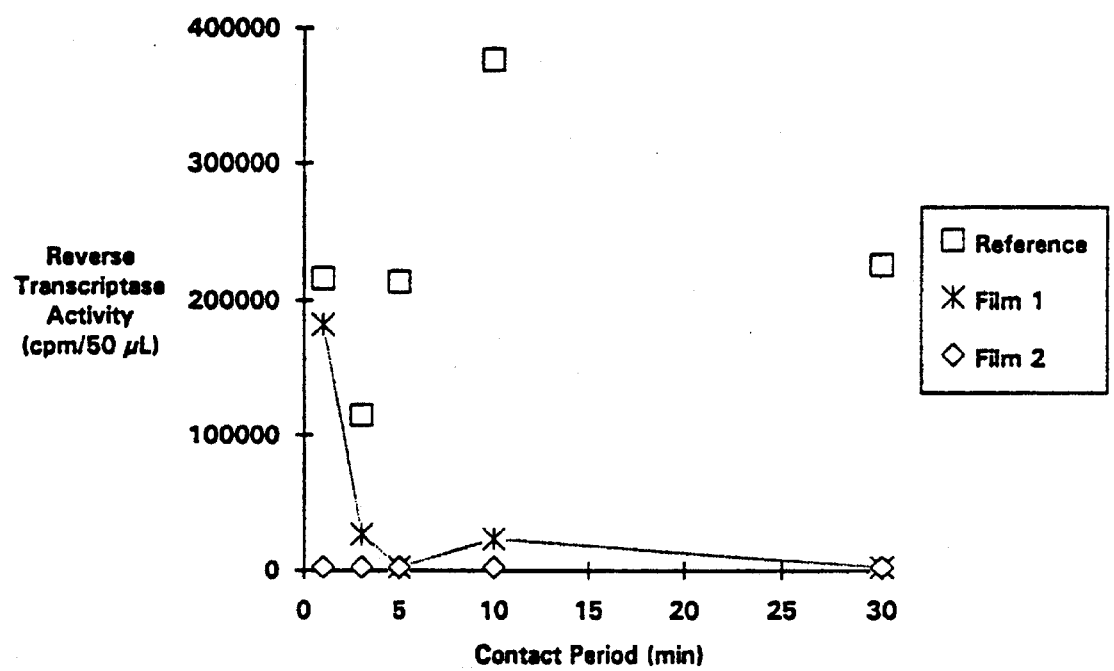
FIG. 7 shows HIV inactivation with polyvinyl chloride film containing 10% of NONOXYNOL-9, (α-(nonylphenyl-w-hydroxypoly (oxy-1-2, ethanediyl).

Experimental points showed on the graph in FIG. 7 represent the residual enzymatic activity of the incubated HIV left for 1, 3, 5, 10 and 30 minutes on the reference and NONOXYNOL-9 (α-(nonylphenyl-w-hydroxypoly (oxy-1-2, ethanediyl) treated films

RESULTS

The nonpermeability of polyvinyl chloride films containing NONOXYNOL-9 (α-(nonylphenyl-w-hydroxypoly (oxy-1-2, ethanediyl) or not containing NONOXYNOL-9 (α-(nonylphenl-w-hydroxypoly (oxy-1-2, ethanediyl) has been demonstrated.

In fact, no trace of antigen p24/25 was observed at time zero and in the different physiological water samples after a contact time of 1, 3, 5, 10 and 30 minutes. The untreated polyvinyl chloride films showed no effect on the infectivity of the HIV for the cell line CD4+. The RTA measured in the culture supernatants is equivalent to the value obtained for experimental HIV cultures for the termination of its infectious titer. Indeed, the infectivity of the experimental HIV left on an untreated polyvinyl chloride film is detected at 50% at a dilution rate of $2.10^{-5}$ (3 wells of positive culture v/s 6) and at 100% until a dilution rate equal to $2.10^{-4}$ after 20 days period of culture.

The study also showed the viricidal activity of the polyvinyl chloride films containing NONOXYNOL-9 (α-(nonylphenyl-w-hydroxypoly (oxy-1-2, ethanediyl) on the infectivity of the different viral samples recovered after 1, 3, 5, 10 and 30 minutes. For HIV incubated on films containing 5% of NONOXYNOL-9 (α-(nonylphenyl-w-hydroxypoly (oxy-1-2, ethanediyl). The RTA measured in the culture supernatants of cells varies from a sample to another independently of the HIV contact time on the external side of the film. An inhibition from 1 to 5 log of the HIV infectivity was observed.

These results can be explained either by a nonhomogenous distribution of the 5% NONOXYNOL-9 (α-(nonylphenyl-w-hydroxypoly (oxy-1-2, ethanediyl) in the polymer or by the display of the 50% concentration limit of NONOXYNOL-9 (α-(nonylphenyl-w-hydroxypoly (oxy-1-2, ethanediyl) active regarding to the high infectious HIV titre.

HIV incubated on films containing 10% NONOXYNOL-9 (α-(nonylphenyl-w-hydroxypoly (oxy-1-2, ethanediyl). The RTA measured in the culture supernatants of cells infected by viral samples recovered after 1 to 30 minutes were very low. An inhibition equal or bigger than 5 log was observed on the infectivity of the HIV incubated on the films containing 10% NONOXYNOL-9 (α-(nonylphenyl-w-hydroxypoly (oxy-1-2, ethanediyl). The short time residual infectivity observed will conclude to a viricidal activity of the NONOXYNOL-9 (α-(nonylphenl-w-hydroxypoly (oxy-1-2, ethanediyl) contained at a rate of 10% in the external side of polyvinyl chloride gloves.

The general conclusion of this study were that 1) the polyvinyl chloride were not permeable to HIV deposited on the external side of the three films; and, the viricidal activity was confirmed (inhibition equal or bigger than 5 log) on the HIV infectious properties when left for 1, 3, 5, 10 and 30 minutes on the external of the film containing 10% NONOXYNOL-9 (α-(nonylphenyl-w-hydroxypoly (oxy-1-2, ethanediyl).

Example 2

Additionally, a number of Anti-HIV producted were tested to determine the concentration of the viricidal agent versus inactivation time. Film 2 of Example 1 was used in this comparison. This comparison shows a short inactivation time at a concentration of about 10%.

TABLE 2

| TYPICAL APPLICATION | PRODUCT | COMPOUNDS | NATURE | CONCENTRATION | INACTIVATION TIME |
|---|---|---|---|---|---|
| SURFACE | A | AMMONIUM SALT DETERGENTS ALDEHYDES | LIQUID | 1% | >5 min. |
| | B | NONIONIC DETERG. AMMONIUM SALT | LIQUID | 0.50% | >5 min. |
| | C | ETHANOL 45% ALDEHYDES AMMONIUM SALT AMMONIUM SALT | SPRAY | 100% | >5 min. |
| INSTRUMENT DISINFECTION | D | ALCOHOL DETERGENTS ALDEHYDES | LIQUID | 1%–2% | >15 min. |
| | E | ALDEHYDES AMMONIUM SALT | LIQUID | 1% | >5 min. |
| | F | GLUTARALDEHYDE | LIQUID | 10% | 15–30 min. |
| HAND DISINFECTION | G | CHLORHEXIDINE ALCOHOLS ALDEHYDES | SPRAY | 2 ml | 30–60 sec. |

VIRICIDAL PRESENT INVENTION NONOXYNOL-9 POLYMER
10%   1 min.
PVC GLOVE

Example 3

In this example, we have tested the passage of HIV-1 through the pinholes of the film and the inactivating effect of the NONOXYNOL-9 (α-(nonylphenyl-w-hydroxypoly (oxy-1-2,ethanediyl) on the HIV-I viral particles which have passed through the films containing NONOXYNOL-9 (α-(nonylphenyl-w-hydroxypoly (oxy-1-2,ethanediyl) or not. In order to carry out such testing, pinholes with an average diameter of 70 μm were made and then controlled with a scanning electron microscope. The size of the hole is comparable with the size of the pinhole occasionally found in gloves.

According to the E.E.C. recommendations relative to the validation of the viral elimination and inactivation processes (ref. III/8115/89-EN; ad hoc working party on biotechnology/pharmacy), a kinetic of viral inactivation has been performed during the experimentation on the films containing or not NONOXYNOL-9 (α-(nonylphenyl-w-hydroxypoly (oxy-1-2,ethanediyl). Samplings were respectively performed after a HIV contact time on the films of 1, 5, 10 and 30 minutes.

The samples used in this study were
films without pinholes and without NONOXYNOL-9 (α-(nonylphenyl-w-hydroxypoly (oxy-1-2,ethanediyl)
films with pinholes and containing 10% NONOXYNOL-9 (α-(nonylphenyl-w-hydroxypoly (oxy-1-2,ethanediyl)
films with pinholes and without NONOXYNOL-9 (α-(nonylphenyl-w-hydroxypoly (oxy-1-2,ethanediyl)

All containing NONOXYNOL-9 (α-(nonylphenyl-w-hydroxypoly (oxy-1-2,ethanediyl) had 10% nonionic detergent and 30% plasticizer.

1. CELLS—T-4 CELLS (Pasteur Institute, biological retrovirus laboratory)

Line of lymphoblate T human cells transformed by HTLV-1 these were grown in a culture medium RPMI 1640 (Flow) added up with 10% of foetal calf serum (Medical and Veterinary supplies ltd U.K.), 2 mm glutamine, 50 μg/ml gentamycin. These cells are used to check the sample infectious rate by HIV-I.

CEM CELLS (ATCC CCL 119)

Line of lymphoblaste T human cells chronically infected by HIV-I. These were grown in a culture medium RPMI 1640 (Flow) added up with 10% of foetal calf serum (Medical and Veterinary supplies ltd. U.K), 2 mm glutamine. Every three or four days, they are maintained to 500000 cells/ml in fresh medium added with 50% CEM non infected cells.

2. HIV-1 (Pasteur Institute, biological retrovirus laboratory)

The HIV-I (LaI strain) was obtained from CEM cell culture supernatant infected by HIV-I. The cells are maintained every three or four days up to 500,000 cells/ml and addition of 50% of uninfected CEM cells. After clarifying, the virus is concentrated by ultracentrifugation at 19000 rpm for three hours (rotor J19) the bottom is resuspended in NTE Buffer (NaCL 0.1M; 0.0001M; Tris 0.01M pH=7.4), aliquoted and stocked at $-75°=-5°$ C. The reverse transcriptase activity (RTA) titer is greater than 1,000,000 cpm/50 μl and its infection titer on MT-4 cells equal to 10,000,000 Infectious Unit/ml (UI/ml).

The films were evaluated as follows:
HIV-I was deposited on the surface of the films.
HIV-I was recovered from the film surface as well as in culture medium placed under the films.

The films were maintained on a petri dish (55 mm diameter) containing 3 ml of culture medium (RPMI-1640 added with 10% foetal calf serum, 2 mm glutamine and 50 μ/ml gentamycin). 1 ml of HIV-I with a titer of 100000 (IU/ml) was placed on the surface of different films. Previously described (point c: samples tested), these films containing NONOXYNOL-9 (α-(nonylphenyl-w-hydroxypoly (oxy-1-2,ethanediyl) or not and were perforated or not. Two films of each type were tested. After 1, 5, 10 and 30 minutes of contact time at room temperature, the viral solutions deposited on the film's surface were collected as well as the culture medium from the petri dish. Sample aliquots were stocked at $-75°+5°$ C. and titrated.

Negative controls:

Culture medium placed on the film without NONOXYNOL-9 (α-(nonylphenyl-w-hydroxypoly (oxy-1-2,ethanediyl) for 30 minutes contact time.

Culture medium present under the film without NONOXYNOL-9 (α-(nonylphenyl-w-hydroxypoly (oxy-1-2,ethanediyl) for 30 minute contact time.

Culture medium placed on the film containing NONOXYNOL-9 (α-(nonylphenyl-w-hydroxypoly (oxy-1-2,ethanediyl) for 30 minutes contact time.

Culture medium present under the film containing NONOXYNOL-9 (α-(nonylphenyl-w-hydroxypoly (oxy-1-2,ethanediyl) for 30 minutes contact time.

Positive controls:

Diluted HIV-I with culture medium at the same dilution rate than those used for the experiment, frozen at $-75°+-5°$ C. then titrated.

HIV-I deposited on the surface of a perforated film without NONOXYNOL-9 (α-(nonylphenyl-w-hydroxypoly (oxy-1-2,ethanediyl) for 1, 5, 10 and 30 minutes, frozen at $-75°+5°$ C. then titrated. To verify the passage of the virus through the pinholes.

HIV-I deposited on the surface of a film without NONOXYNOL-9 (α-(nonylphenyl-w-hydroxypoly (oxy-1-2,ethanediyl) and pinholes for 30 minutes, frozen at $-75°+5°$ C. then titrated. To verify the film toxicity on the virus.

HIV-I deposited on the surface of a film containing NONOXYNOL-9 (α-(nonylphenyl-w-hydroxypoly (oxy-1-2,ethanediyl) but without pinholes for 30 minutes frozen a $-75°+-5°$ C. then titrated. To verify the viricidal effect of the NONOXYNOL-9 (α-(nonylphenyl-w-hydroxypoly (oxy-1-2,ethanediyl) in the experiment conditions.

1) Infectivity of the samples for the MT-4 cells: monitored by the measurement of the reverse transcriptase activity.

The results reported in Table 1 A show that the virus passes through the pinholes performed in the PVC films without NONOXYNOL-9 (α-(nonylphenyl-w-hydroxypoly (oxy-1-2,ethanediyl). In fact, the HIV-I was detected in the culture medium placed under the film. The quantity of infectious virus increased as a function of the contact time, from 100 Infectious Unit/ml after 1 minute of contact to 10,000 Infectious Unit/ml after 30 minutes. On the other hand, after the passage through the pinholes of a film containing NONOXYNOL-9 (α-(nonylphenyl-w-hydroxypoly (oxy-1-2,ethanediyl) the infectious titer found after a contact of 1 minute, in the culture medium placed under the films, was lower than 10 IU/ml, according to the detection level of the method used (Table 1B).

The virus were placed on the surface of a film containing no NONOXYNOL-9 (α-(nonylphenyl-w-hydroxypoly (oxy-1-2,ethanediyl) remains infectious whether or not the film is perforated (Table 1A). Indeed, the virus infectivity reached 10000 to 100000 IU/ml whatever the contact time with the film.

The virus deposited on the surface of a perforated film containing NONOXYNOL-9 (α-(nonylphenyl-w-hydroxypoly (oxy-1-2,ethanediyl) looses its infectivity after 1 minute of contact with the first film and 5 minutes of contact with the second film (Table 1 B). This difference in the action time between the two films treated under the same conditions could be explained by the diferrence in the size of the pinholes performed which can vary around 70 μm. As the samples are treated in sequence, however a difference of a few seconds in the contact time cannot be excluded.

We have checked that nonperforated films are nonpermeable to the HIV-I virus (Table 1A and 1B). After a contact of 30 minutes, no infectious particles were found in the culture medium beneath the films containing NONOXYNOL-9 (α-(nonylphenyl-w-hydroxypoly (oxy-1-2,ethanediyl) or not.

We also checked the viricidal effect of the NONOXYNOL-9 (α-(nonylphenyl-w-hydroxypoly (oxy-1-2, ethanediyl) on the HIV-I virus. Left for a 30 minute contact time on two films containing NONOXYNOL-9 (α-(nonylphenyl-w-hydroxypoly (oxy-1-2,ethanediyl), the virus is totally inactivated (Table 1B). On the other hand, the films which do not contain NONOXYNOL-9 (α-(nonylphenyl-w-hydroxypoly (oxy-1-2,ethanediyl) present after 30 minutes, an unchanged infectious titer (Table 1B).
2) Infectivity of the samples for the MT-4 cells: monitored by the measurement of the antigen p24.

Figure 8:
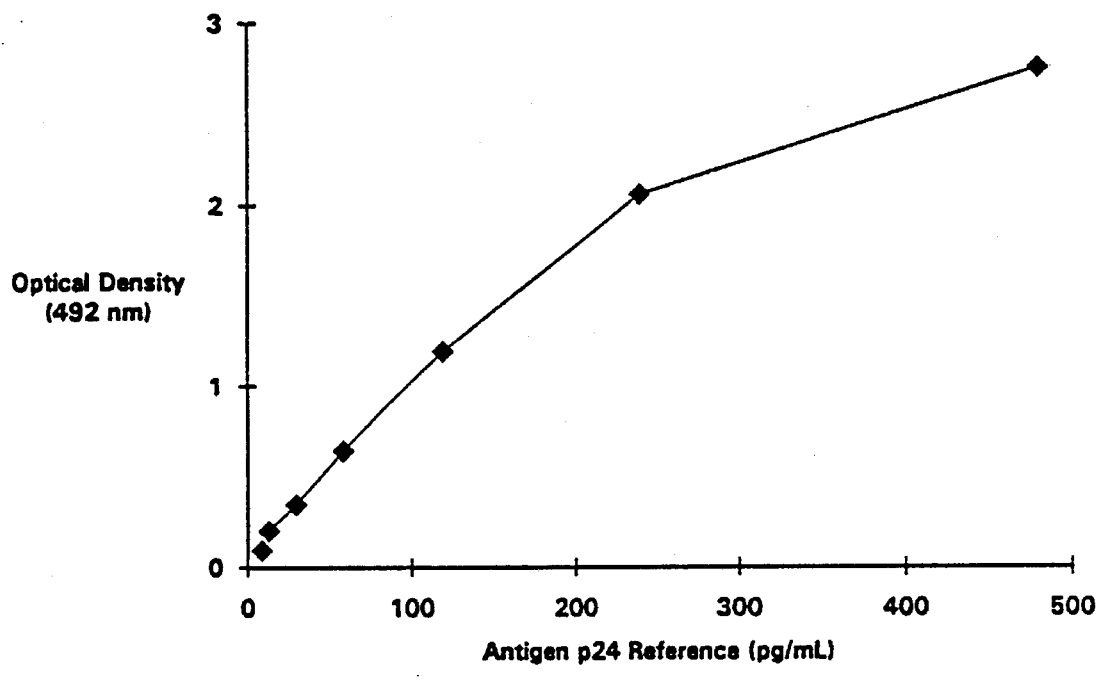
FIG. 8 shows the reference curve for the dosage of p24 antigen.

In order to ensure the absence of viral particles in the culture medium present under the films containing NONOXYNOL-9 (α-(nonylphenyl-w-hydroxypoly (oxy-1-2, ethanediyl), the dosage of the p24 antigens was performed in the supernatants of the infectivity tests at days: 0, 4 and 7. The p24 antigen was quantified thanks to the calibration curve reported on FIG. 8.

Table 2 shows the results obtained for the tested samples corresponding to contact time from 1 and 30 minutes with the films. A decrease of p24 antigen quantity was observed as a function of the time in the supernatants of the test. For the first film tested with a contact time of 1 minute, the p24 antigens decrease from 52 pg/ml on day 0 to less than 2.5 pg/ml (detection level of the method) on day 7th (Table 2). The second film tested, in the same conditions, p24 antigen quantity decreases from 141.5 to 4 pg/ml respectively on days 0 and 7. The same type of result is observed, for the virus left for a contact time of 30 minutes with the films. These results show the passage of a few residual viral particles in the petri dish put beneath the perforated film containing NONOXYNOL-9 (α-(nonylphenyl-w-hydroxypoly (oxy-1-2,ethanediyl).

Dosages of p24 antigens were also performed in the supernatants (days 4 and 7) of the infectivity tests presented in Table 1 for the samples collected on the perforated film containing NONOXYNOL-9 (α-(nonylphenyl-w-hydroxypoly (oxy-1-2,thanediyl), after a contact of 30 minutes. In Table 2, we observe a significant presence of p24 antigens in the supernatant which decreases over the time of culture being not negligible on day seven.

To confirm the absence of infectious virus in the supernatants (day four), these supernatants were used to re-infect MT-4 cells. This reinfection should, indeed, allow to amplify the potential infectious viral particles, eventually present in the supernatants, using the cellular culture. The viral monitoring in the supernatants of this second infectivity test on MT-4 cells has been performed by the measurement of the Reverse Transcriptase Activity (RTA).

Table shows that the virus present in the supernatants (day four) of the first infectivity test is not infectious for the MT-4 cells as less than 10 IU/ml are detected during the second test on the same cells (Table 3).

In this example, we have showed that the infectious particles HIV-I pass through the pinholes made in the films which do not contain NONOXYNOL-9 (α-(nonylphenyl-w-hydroxypoly (oxy-1-2,ethanediyl). On the other hand, no HIV-I infectious particles at all is detected after the passage of the virus through the pinholes of both film tested which contain NONOXYNOL-9 (α-(nonylphenyl-w-hydroxypoly (oxy-1-2, ethanediyl).

The film with no pinholes do not allow the passage of the virus which still remains infectious on the surface of the films not containing NONOXYNOL-9 (α-(nonylphenyl-w-hydroxypoly (oxy-1-2, ethanediyl).

The viricidal activity of the NONOXYNOL-9 (α-(nonylphenyl-w-hydroxypoly (oxy-1-2,ethanediyl) is as well efficient as on the virus passing through the pinholes of the films than on the virus remaining on the surface. Indeed, the virus remaining on the surface of one of both films tested which contain NONOXYNOL-9 (α-(nonylphenyl-w-hydroxypoly (oxy-1-2,ethanediyl), is already inactivated after one minute of contact time and after five minutes of contact time for the second film tested in the same conditions.

It appears that NONOXYNOL-9 (α-(nonylphenyl-w-hydroxypoly (oxy-1-2,ethanediyl) incorporated into the films has a sufficient viricidal activity to inactivate the infectious HIV-I which could pass through the pinholes of the film.

Although the invention has been described primarily in connection with special and preferred embodiments, it will be understood that it is capable of modification without departing from the scope of the invention. The following claims are intended to cover all variations, uses, or adaptations of the invention, following, in general, the principles thereof and including such departures from the present disclosure as come within known or customary practice in the field to which the invention pertains, or as are obvious to persons skilled in the field.

We claim:

1. Polymeric material containing a pool of viricidal agents made by the process comprising; mixing a molten blend of polyvinyl chloride and a viricidal nonionic surfactant having Hydrophilic Lipophilic Balance of between 12 and 20, said compound consisting of: $R_1$—O—(($CH_2$) $a_i$—O)$_n$—$R_2$ where $R_1$ is a saturated or unsaturated hydrocarbon radical, the constituent elements selected from the group consisting of carbon, hydrogen or oxygen; $a_i$ is, for i=to $_{n'}$ an integer greater or equal to 2; $R_2$ is an organic radical, the constituent elements selected from the group consisting of carbon, hydrogen or oxygen and n is an integer selected so that the Hydrophilic Lipophilic Balance of said compound is between 12 and 20, the improvement comprising adding a sufficient amount of a plasticizer having a molecular weight of at least 300 to the molten blend to increase the viricidal activity of said compound.

2. The material of claim 1 wherein said viricidal agents act on enveloped viruses.

3. The material of claim 1 wherein said viricidal compound is (a (nonylphenyl)-w-hydroxypoly (oxy-1-2, ethanediyl).

4. The material of claim 1 wherein said plasticizer is di-iso nonyl phthalate.

\* \* \* \* \*